United States Patent [19]

Liu

[11] Patent Number: 5,707,608
[45] Date of Patent: Jan. 13, 1998

[54] METHODS OF MAKING LIPOSOMES CONTAINING HYDRO-MONOBENZOPORPHYRIN PHOTOSENSITIZER

[75] Inventor: Ron Liu, North Chicago, Ill.

[73] Assignee: QLT PhotoTherapeutics, Inc., Vancouver, Canada

[21] Appl. No.: 510,573

[22] Filed: Aug. 2, 1995

[51] Int. Cl.$^6$ .................. A61K 49/00; G01N 31/00; G01N 33/48
[52] U.S. Cl. ................ 424/9.61; 424/9.6; 424/9.1
[58] Field of Search .................. 424/1.11, 1.65, 424/9.1, 400, 450, 1.21, 9.3, 9.56, 9.361, 9.362, 9.6, 9.61; 428/402.2, 402.24; 264/4.1; 427/213.3

[56] References Cited

U.S. PATENT DOCUMENTS

| | | |
|---|---|---|
| 4,485,806 | 12/1984 | Akers . |
| 4,500,507 | 2/1985 | Wong . |
| 4,517,762 | 5/1985 | Venetz . |
| 4,577,636 | 3/1986 | Spears . |
| 4,649,151 | 3/1987 | Dougherty et al. . |
| 4,753,958 | 6/1988 | Weinstein et al. . |
| 4,776,991 | 10/1988 | Farmer et al. . |
| 4,866,168 | 9/1989 | Dougherty et al. . |
| 4,883,790 | 11/1989 | Levy et al. . |
| 4,889,129 | 12/1989 | Dougherty et al. . |
| 4,920,143 | 4/1990 | Levy et al. . |
| 4,932,934 | 6/1990 | Dougherty et al. . |
| 4,933,121 | 6/1990 | Law et al. ............... 424/450 |
| 5,010,073 | 4/1991 | Kappas et al. . |
| 5,053,423 | 10/1991 | Liu ............... 424/450 |
| 5,214,036 | 5/1993 | Allison et al. ............... 424/450 |
| 5,238,940 | 8/1993 | Liu et al. ............... 424/450 |
| 5,270,053 | 12/1993 | Schneider et al. . |
| 5,389,378 | 2/1995 | Madden ............... 424/450 |
| 5,422,362 | 6/1995 | Vincent et al. ............... 424/450 |

FOREIGN PATENT DOCUMENTS

| | | |
|---|---|---|
| 569113 | 5/1993 | European Pat. Off. . |

OTHER PUBLICATIONS

Kessel et al (Eds), "Porphyrin Photosensitization", Plenum Press (1983).

Diamond, et al., "Photodynamic Therapy of Malignant Tumours," *Lancet*, 2:1175–77 (1972).

Dougherty et al., "Photoradiation Therapy of Human Tumors, in *The Science of Photo Medicine*", 625–38 (Regan et al., eds. 1982).

Dougherty et al., "Photosensitizers," in *Cancer: Principles and Practice of Oncology*, 1836–44 (DeVita Jr., et al., eds. 1982).

Johnson et al., "Comparison studies of selected prophyrin photosensitizers," *Proc. Photodynamic Therapy: Mechanisms II*, Proc. SPIE–Int. Soc. Opt. Eng., 1203:266–80 (1990).

Jori et al., "Preferential delivery of liposome–incorporated porphyrins to neoplastic cells in tumour–bearing rats," *Br. J. Cancer*, 48:307–309 (1983).

Lipson et al., "The Use of a Derivative of Hematoporphyrin in Tumour Detection," *J. Natl. Cancer Inst.*, 26:1–8 (1961).

Milanesi et al., "Photokinetic and ultrastructural studies on porphyrin photosensitization of HeLa cells," *Int. J. Radiat. Biol.*, 55:59–69 (1989).

Ricchelli, "Liposomes as carriers of hydrophobic photosensitizers in vivo: increased selectivity of tumor targeting," *New Directions in Photodynamics Therapy*, 847:101–106 (1987).

Schweitzer et al., "Photodynamic therapy for treatment of AIDS–related oral Kaposi's sarcoma," *Otolaryngology—Head and Neck Surgery*, 102:639–49 (1990).

Spikes et al., "Photodynamic Therapy of Tumours and Other Diseases Using Porphyrins," *Lasers in Medical Science*, 2:3–15 (1987).

Weishaupt et al., "Identification of Singlet Oxygen as the Cytotoxic Agent in Photo–inactivation of a Murine Tumor," *Cancer Research*, 36:2326–29 (1976).

Zhou et al., "An Ultrastructural Comparative Evaluation of Tumors Photosensitized by Porphyrins Administered in Aqueous Solution, Bound to Liposomes or to Lipoproteins," *Photochemistry and Photobiology*, 48:487–92 (1988).

*Primary Examiner*—John Kight
*Assistant Examiner*—Dameron Jones
*Attorney, Agent, or Firm*—Morrison & Foerster LLP

[57] ABSTRACT

Liposomal compositions containing green porphyrins as photosensitizers are improved by enhancing the ratio of phospholipid to photosensitizer and by conducting the hydration an sizing of the liposomes in the composition at low temperature.

24 Claims, 6 Drawing Sheets

STEP 1: PHOTOSENSITEP IS SQUEEZED OUT OF
THE LIPID BILAYER AT HIGH TEMPERATURE

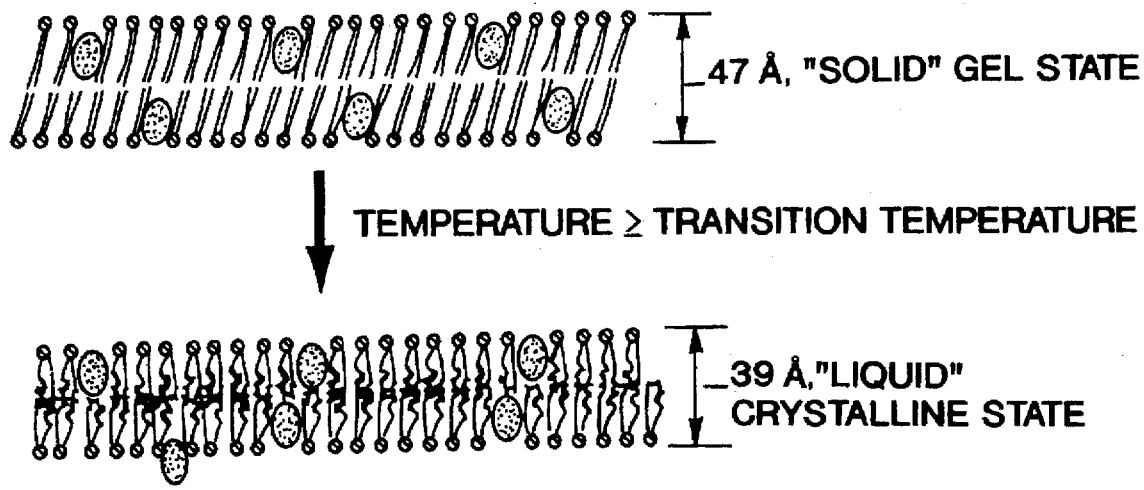

STEP 2: AGGREGATION OF TWO PHOTOSENSITIZER
SQUEEZED-OUT VESICLES
(PICTURE SHOWS ONLY PORTION
OF THE OUTER BILAYER OF VESICLES).

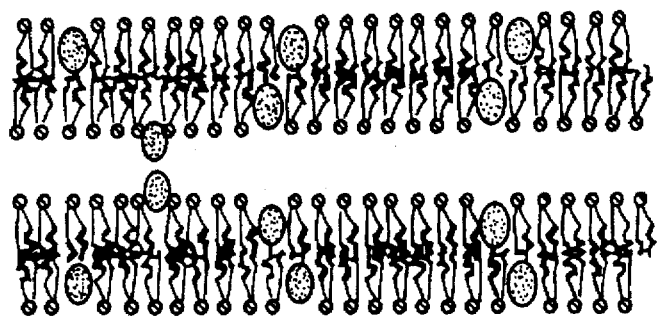

 = LIPID MOLECULE WITH THE ALL-TRANS STRAIGHT
CHAIN CONFIGURATION AT LOW TEMPERATURE.

 = LIPID MOLECULE WITH THE GAUCHE
CONFIGURATION AT HIGH TEMPERATURE.

 = HYDROPHOBIC PHOTOSENSITIZER MOLECULE.

FIG. 4

METHODS OF MAKING LIPOSOMES CONTAINING HYDRO-MONOBENZOPORPHYRIN PHOTOSENSITIZER

FIELD OF THE INVENTION

The invention relates to improved pharmaceutical compositions comprising liposomes incorporating porphyrin photosensitizers and methods for making these liposomes. Specifically, the invention is directed to pharmaceutical liposome compositions comprising a hydro-monobenzoporphrin photosensitizer and a mixture of phospholipids comprising egg phosphatidyl glycerol ("EPG") and dimyristoyl phosphatidyl choline ("DMPC") in a photosensitizer- :phospholipid molar ratio of about 1:7.0 or more phospholipid. The liposomes are made in such a way that the particle size range is about 150 to 300 nm.

The photosensitizing liposome compositions are useful to mediate the destruction of unwanted cells or tissues or other undesirable materials by irradiation or to detect their presence through fluorescence. Particularly preferred hydro-monobenzoporphyrin photosensitizers used in the practice of this invention include those having one or more light absorption maxima in the range of 670–780 nm.

DESCRIPTION OF THE RELATED ART

The use of porphyrin compounds and, in particular hematoporphyrin and hematoporphyrin derivatives (HPD), has been known for some time to be useful systemically, when combined with light, for the treatment and diagnosis of malignant cells. The porphyrins have a natural tendency to "localize" in malignant tissue, where they absorb light at certain wavelengths when irradiated, thus providing a means to detect the tumor by the location of the fluorescence. Accordingly, preparations containing the porphyrins are useful in the diagnosis and the detection of tumor tissue. (See, e.g. "Porphyrin Photosensitization", Plenum Press (Kessel et al. eds. 1983)). In addition, When exposed to light at an appropriate wavelength, the porphyrins have the ability to exhibit a cytotoxic effect on the cells or other tissues in which they are localized. (See, e.g., Diamond et al., *Lancet*, 2:1175–77 (1972); Dougherty et al., "The Science of Photo Medicine", 625–38 (Regan et al., eds. 1982); and Dougherty et al., "Cancer: Principles and Practice of Oncology", 1836–44 (DeVita Jr. et al. eds. 1982)). It has been postulated that the cytotoxic effect of porphyrins is due to the formation of singlet oxygen when exposed to light (Weishaupt et al., *Cancer Research*, 36:2326–29 (1976)). The successful treatment of AIDS-related oral Kaposi's Sarcoma with a purified form of HPD, Photofrin®, porfimer sodium, was described by Schwietzer et al., *Otolaryngology—Head and Neck Surgery*, 102:639–49 (1990).

In addition to systemic use for the diagnosis and treatment of tumors, the porphyrins can be used in a variety of other therapeutic applications. For example, photosensitizers are useful in the detection and treatment of atherosclerotic plaques, as disclosed in U.S. Pat. Nos. 4,517,762 and 4,577,636. U.S. Pat. Nos. 4,500,507 and 4,485,806 describe the use of radio-labeled porphyrin compounds for tumor imaging. Porphyrin compounds have also been used topically to treat various skin diseases, as disclosed in U.S. Pat. No. 4,753,958.

A number of porphyrin photosensitizer preparations have been disclosed for therapeutic applications. A photosensitizer preparation widely used during the early stages of photodynamic therapy both for detection and treatment was a crude derivative of hematoporphyrin, also called hematoporphyrin derivative ("HPD") or Lipson derivative, prepared as described by Lipson et al., *J, Natl. Cancer Inst.*, 26:1–8 (1961). A purified form of the active component(s) of HPD was prepared by Dougherty and co-workers by adjustment of the pH to cause aggregation, followed by recovery of the aggregate, as disclosed in U.S. Pat. Nos. 4,649,151; 4,866,168; 4,889,129; and 4,932,934. A purified form of this product is being used clinically under the trademark Photofrin®, porfimer sodium.

Of particular interest in the context of the present invention is a group of modified porphyrins, known as "green porphyrins" (Gp), having one or more light absorption maxima between about 670–780 nm. These Gp compounds have been shown to confer cytotoxicity against target cells at concentrations lower than those required for hematoporphyrin or HPD. Gp compounds can be obtained using Dieis-Alder reactions of protoporphyrin with various acetylene derivatives under the appropriate conditions. Preferred forms of Gp are the hydro-monobenzoporphyrin derivatives ("BPD's"). The preparation and use of the Gp and BPD compounds are disclosed in U.S. Pat. Nos. 4,920,143 and 4,883,790, hereby incorporated by reference into the disclosure of the present application.

While the porphyrin compounds have a natural ability to localize in neoplastic tissue, while being cleared from the normal surrounding tissue, the selectivity of the porphyrin photosensitizers is still somewhat limited. Because tumor tissue generally includes a number of different components, such as malignant cells, a vascular system, macrophages, fibroblasts, etc., the distribution of the photosensitizer within tumor tissue may be highly heterogeneous. This is especially true for those photosensitizers that are not homogeneous and that contain a mixture of components having different degrees of hydro- or liposolubility. Zhou et al., *Photochemistry and Photobiology*, 48:487–92 (1988). The low selectivity of some of these agents as tumor localizers may lead to side-effects, such as an undesirably systemic hypersensitivity to light. Therefore, an active area of research has been to increase the tumor selectivity of known porphyrin photosensitizers and to identify those porphyrin photosensitizers that may exhibit greater tumor-selectivity. In general, photosensitizers that are more lipophilic tend to exhibit greater tumor-targeting capability. Spikes et al., *Lasers in Medical Science*, 2:3, 3–15 (1986).

It has recently been shown that the encapsulation of certain drugs in liposomes, prior to administration, has a marked effect on the pharmacokinetics, tissue distribution, metabolism and efficacy of the therapeutic agent. In an effort to increase the tumor selectivity of porphyrin photosensitizers, porphyrin compounds have been incorporated into unilamellar liposomes, resulting in a larger accumulation and a more prolonged retention of the photosensitizer by both cultured malignant cells and in experimental tumors in vivo. Jori et al., *Br. J. Cancer*, 48:307–309 (1983); Cozzani et al., *In Porphyrins in Tumor Phototherapy*, 177–183, Plenum Press (Andreoni et al. eds. 1984). This more efficient targeting of tumor tissues by liposome-associated porphyrins may be due in part to the specific delivery of phospholipid vesicles to serum lipoproteins, which have been shown to interact preferentially with hyperproliferative tissue, such as tumors, through receptor-mediated endocytosis. In this manner, the selectivity of porphyrin uptake by tumors has been increased, as compared with photosensitizers dissolved in aqueous solution. See Zhou et al., supra.

Accordingly, hematoporphyrin and hematoporphyrin dimethyl esters have been formulated in unilamellar vesicles of dipalmitoyl phosphatidyl choline (DPPC) and liposomes of dimyristoyl (DMPC) and distearoyl phosphatidyl choline (DSPC). Zhou et al., supra; Ricchelli, *New Directions in Photodynamic Therapy*, 847:101–106 (1987); Milanesi, *Int. J. Radiat. Biol.*, 55:59–69 (1989). Similarly, HP, Photofrin®, porfimer sodium, and tetrabenzoporphyrins have been formulated in liposomes composed of egg phosphatidyl choline (EPC). Johnson et al., *Proc. Photodynamic Therapy: Mechanisms II*, Proc. SPIE-Int. Soc. Opt. Eng., 1203:266–80 (1990). Further, freeze-dried pharmaceutical formulations comprising a porphyrin photosensitizer, a disaccharide or polysaccharide, and one or more phospholipids (such as EPG and DMPC) have been made. These formulations form liposomes containing an effective amount of porphyrin photosensitizer upon reconstitution with a suitable aqueous vehicle and are described in Desai et al., copending U.S. application Ser. No. 08/489,850 filed 13 Jun. 1995.

When the process of Desai et al. is applied to large batches, e.g., 5 to 10 liters or greater, up to about 100–200 liters, some decrease in potency has been observed due to loss of product during the sterile filtration step. The loss is related to the particle size reduction step. Thus, due to the importance of photodynamic therapy in the treatment of cancer, there is a continuing need to identify new photosensitizer formulations that are not only stable and capable of selective delivery of a photosensitizer to target tissues, but also that are easily manufactured on a large scale.

Farmer et al., U.S. Pat. No. 4,776,991 discloses the large-scale encapsulation of hemoglobin in liposomes having a narrow liposome size distribution comprising, as phospholipids, (1) hydrogenated soy phosphatidyl choline ("HSPC"; approximate composition 85% distearoyl phosphatidyl choline and 15% dipalmitoyl phosphatidyl choline);

(2) cholesterol;

(3) negatively charged DMPC; and (4) alpha-tocopherol.

(Farmer et al., column 3, lines 52–69.) These lipids are mixed in chloroform to form a solution; the chloroform is evaporated away to form a lipid film; and sterile hemoglobin is added to the film with gentle agitation at 35° C. (30°–37° C.) for 45 minutes to form multilamellar liposomes. Rotary agitation of the liposomes is continued at 4° C. (2°–6° C.) for 10–16 hours, and the liposomes are forced through a Microfluidizer™ to break multilamellar liposomes and produce large unilamellar liposomes. The interaction cheer of the Microfluidizer™ is maintained at 5°–7° C. (Column 4, lines 1–14; column 7, lines 3–9 and 19–21.) The lipids chosen to make the liposomes, however, must be temporarily shrunk by hyperosmotic shock with added saline prior to sterilization by pressure filtration through a standard 0.22 µm sterilizing filter. (Column 4, line 18–22; column 9, lines 55–58.)

Kappas et al., U.S. Pat. No. 5,010,073 issued 23 Apr. 1991, discloses the preparation of liposomes containing a metalloporphyrin with egg phosphatidyl choline ("EPC") being used as the lipid. The EPC is dissolved in chloroform, the metalloporphyrin is added, and the solution is evaporated to dryness. Phosphate buffered saline at room temperature is used to hydrate the lipid film, and the mixture is "vortexed vigorously." Solids are collected by centrifuging at 4° C. The weight ratio of EPC to metalloporphyrin may be greater than 10. (Kappas et al., column 6, lines 46–65.) However, Kappas et al. recommends that the resulting metalloporphyrin liposomes be sonicated prior to injection to prevent the production of large aggregates. (Column 6, line 66 through column 7, line 1.)

Schneider et al., U.S. Pat. No. 5,270,053 issued 14 Dec. 1993, discloses liposome formulations said to be free of solid particles and larger lipid aggregates. (Schneider et al., column 3, lines 52–54.) However, the presence of a specific synthetic lipid is required. (Column 2, lines 51–66.) For example, in Example 21, at columns 13 and 14, 50 grams of a mixture of two such synthetic lipids are dissolved in tertiary butanol, which is then mixed with a solution of 0.5 g zinc-phthalocyanine. Using a dynamic mixer, the solution is mixed with 10 liters of lactose medium cooled to 4° C. to produce a blue, slightly opalescent dispersion. The separation and isolation of large liposomes from the small liposomes is performed, when necessary, by conventional separation methods such as gel filtration or sedimentation. (Column 7, lines 11–17.)

Thus, there remains a need for a large-scale method to produce DMPC/EPG liposomes containing a photosensitizer in small enough particle sizes that large quantities of pharmaceutical compositions containing the liposomes are easily aseptically filtered through standard 0.22 µm sterilizing filters in an efficient manner and without the need for preparing the synthetic lipids of Kappas et al.

SUMMARY OF THE INVENTION

The present invention involves a method for making a pharmaceutical composition containing liposomes. The liposomes comprise a therapeutically acceptable amount of a hydro-monobenzoporphyrin photosensitizer and a mixture of phospholipids comprising egg phosphatidyl glycerol ("EPG") and dimyristoyl phosphatidyl choline ("DMPC"). The method of making such liposomes comprises the steps of:

a. combining the photosensitizer and the phospholipids in a molar ratio of about 1:7.0 or more phospholipid in the presence of an organic solvent;

b. removing the organic solvent to form a lipid film;

c. hydrating the lipid film with an aqueous solution at a temperature below 30° C., to form coarse liposomes containing a photosensitizer-phospholipid complex; and d. homogenizing or reducing the particle size of the coarse liposomes to a particle size range of about 150 to 300 nm at a temperature below about 30° C.

The hydrating and homogenizing/reducing steps "c." and "d." of the invention are preferably performed at a temperature below the glass transition temperature of the photosensitizer:DMPC/EPG phospholipid mixture complex.

Maintaining the hydration temperature and the homogenizing/reducing step at a temperature below 30° C. would not have been expected to produce smaller particle sizes. In fact, the invention is contrary to the conventional wisdom that small particle sizes are achieved by increasing rather than decreasing these temperatures. See, e.g., M. Lee et al., "Size Distribution of Liposomes by Flow Field-Flow Fractionation", *J. Pharm. & Biomed. Analysis*, 11:10, 911–20 (1993), equation (6) showing particle diameter "d" as inversely related to temperature "T", and FIG. 6b showing liposome preparation I (prepared at about 70° C.) having smaller particle sizes than preparation II (prepared at about 23° C.).

The invention also contemplates the pharmaceutical compositions themselves, which comprise liposomes including a hydro-monobenzoporphyrin photosensitizer and a mixture of DMPC and EPG phospholipids in a photosensitizer-phospholipid molar ratio of about 1:7.0 or more phospholipid, and which have a particle size of about 150 to 300 nm.

These liposome compositions provide nearly 100% encapsulation of the hydro-monobenzoporphyrin photosensitizer, which can be expensive and usually requires a complicated synthetic procedure to produce. Thus, there is no reworking necessary and very little waste of the photosensitizer. In addition, due to their small particle size, the present liposomes exhibit the improved filterability important in producing large-scale batches of a 500 ml to liter or more, as well as improved retention of photosensitizer potency.

BRIEF DESCRIPTION OF THE DRAWINGS

Other objects, features, and advantages will occur from the following descriptions of the various embodiments and the accompanying drawings, in which:

FIG. 4 shows a proposed mechanism for the effect of temperature on the aggregation of a hydro-monobenzoporphyrin photosensitizer.

DETAILED DESCRIPTION OF THE INVENTION

The present invention relates to a pharmaceutical liposome formulation of a hydro-monobenzoporphyrin photosensitizer for use in the photodynamic therapy or diagnosis of tumors, or for a variety of other therapeutic applications. Liposomes are completely closed, lipid bilayer membranes that contain an entrapped aqueous volume. Typically, liposomes are formed spontaneously upon the addition of an aqueous solution to a dry lipid film.

The liposomes of the invention may be unilamellar vesicles having a single membrane bilayer or multilamellar vesicles having multiple membrane bilayers, each bilayer being separated from the next by an aqueous layer. A liposome bilayer is composed of two lipid monolayers having a hydrophobic "tail" region and a hydrophilic "head" region. The structure of the membrane bilayer is such that the hydrophobic (nonpolar) "tails" of the lipid monolayers orient themselves towards the center of the bilayer, while the hydrophilic "heads" orient themselves toward the aqueous phase. Either unilamellar or multilamellar or other types of liposomes may be used in the practice of the present invention.

In a liposome-drug delivery system, a hydrophilic therapeutic agent can be entrapped in the aqueous phase of the liposome and then administered to the patient. Alternatively, if the therapeutic agent is lipophilic, it may associate with the lipid bilayer. Liposomes may be used to help "target" a drug to an active site or to solubilize hydrophobic drugs for parenteral administration. Typically, the hydro-monobenzoporphyrin photosensitizer of the invention is relatively hydrophobic and forms a stable photosensitizer-lipid complex.

The liposomes of the present invention possess certain attributes that make them well-suited for delivering a hydro-monobenzoporphyrin photosensitizer. The liposomes formed in the present invention are "fast breaking" in that the photosensitizer-liposome combination is stable in vitro but, when administered in vivo, the photosensitizer is rapidly released into the bloodstream where it associates with serum lipoproteins. It is believed that this inhibits the photosensitizer from being accumulated in non-target tissues such as the liver.

Photosensitizers

The photosensitizers useful in the practice of this invention include the hydro-monobenzoporphyrins (the so-called "green porphyrins" or "Gp" compounds) disclosed in U.S. Pat. Nos. 4,920,143 and 4,883,790. Typically, these compounds have one or more light absorption maxima between about 670–780 nm and are poorly water-soluble (less than 1 mg/ml) or water-insoluble. Gp is preferably selected from the group consisting of those compounds having one of the formulae 1–6 set forth in FIG. 1, mixtures thereof, and the metalated and labeled forms thereof.

Figure 1A:
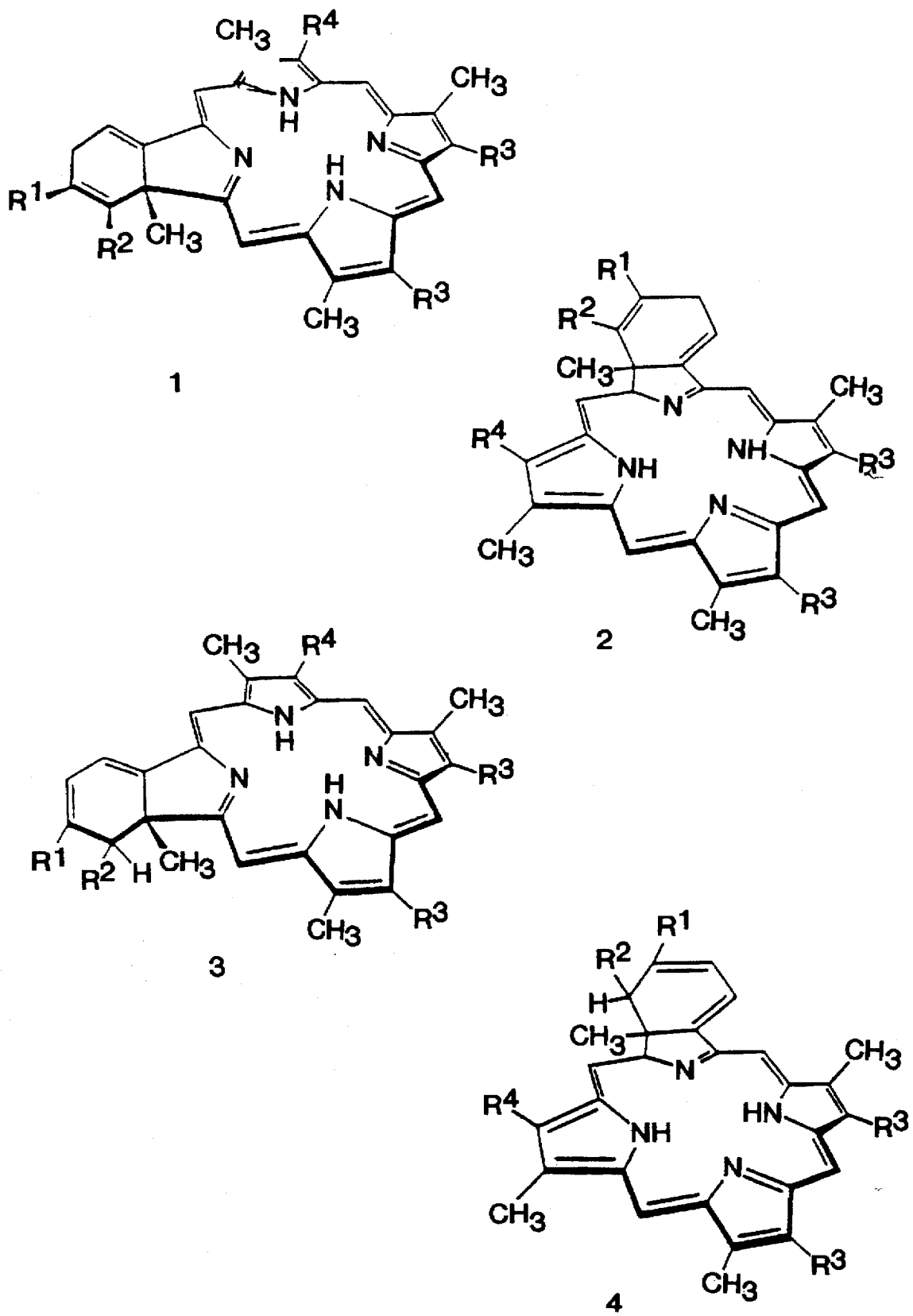
FIG. 1 shows the structure of green porphyrin (Gp) compounds used in the liposomal formulations of the invention.
Figure 1B:
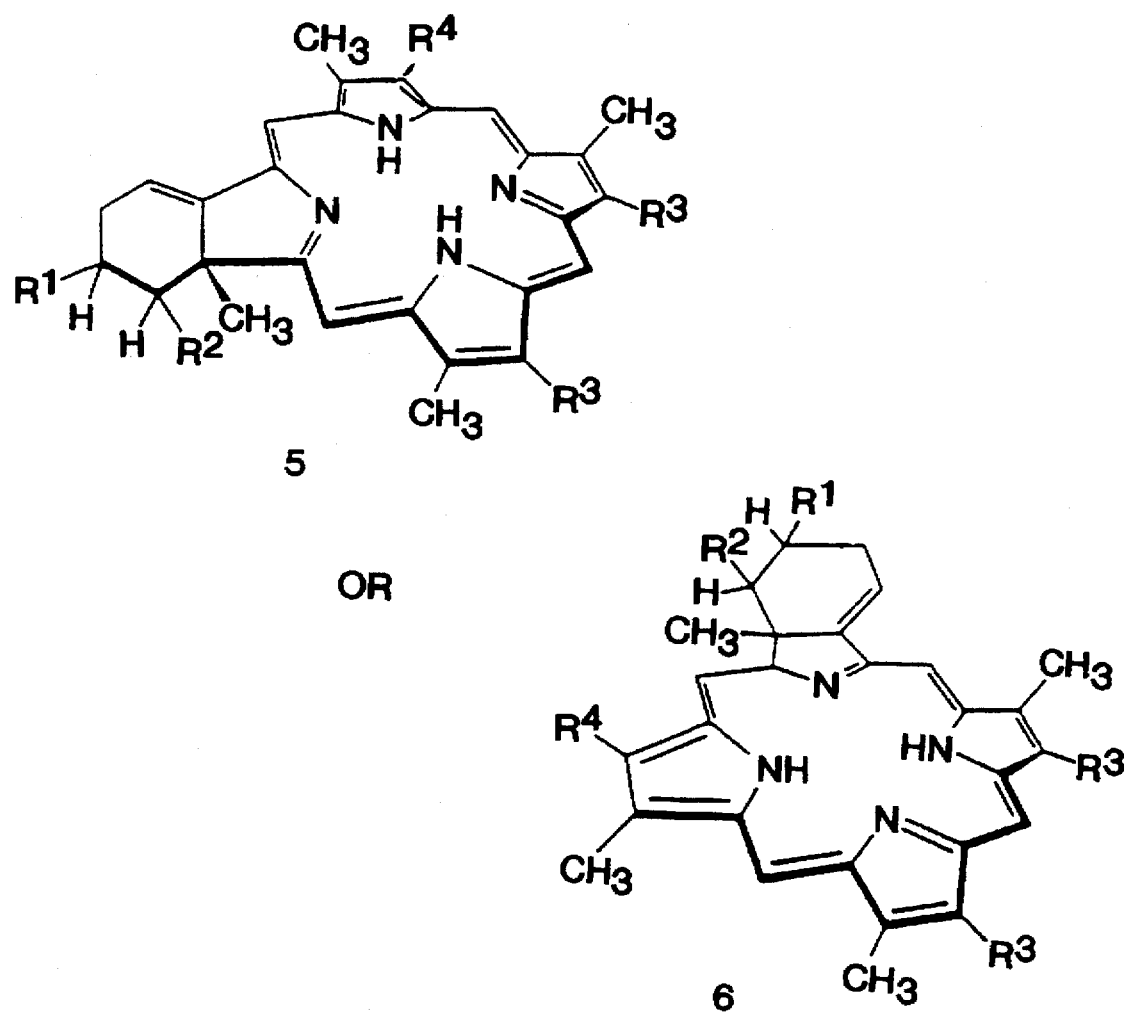

In FIG. 1, $R^1$ and $R^2$ can be independently selected from the group consisting of carbalkoxy (2–6C), alkyl (1–6C) sulfonyl, aryl (6–10C) sulfonyl, aryl (6–10C), cyano, and $-CONR^5CO-$ wherein $R^5$ is aryl (6–10C) or alkyl (1–6C). Preferably, however, each of $R^1$ and $R^2$ is carbalkoxy (2–6C).

$R^3$ in FIG. 1 can be independently carboxyalkyl (2–6C) or a salt, amide, ester or acylhydrazone thereof, or is alkyl (1–6C). Preferably $R^3$ is $-CH^2CH^2COOH$ or a salt, amide, ester or acylhydrazone thereof.

$R^4$ is $-CHCH_2$; $-CHOR^{4'}$ wherein $R^{4'}$ is H or alkyl (1–6C), optionally substituted with a hydrophilic substituent; $-CHO$; $-COOR^{4'}$; $CH(OR^{4'})CH_3$; $CH(OR^{4'})CH_2OR^{4'}$; $-CH(SR^{4'})CH_3$; $-CH(NR^{4'}{}_2)CH_3$; $-CH(CN)CH_3$; $-CH(COOR^{4'})CH_3$; $-CH(OOCR^{4'})CH_3$; $-CH(halo)CH_3$; $-CH(halo)CH_2(halo)$; an organic group of <12C resulting from direct or indirect derivatization of a vinyl group; or $R^4$ consists of 1–3 tetrapyrrole-type nuclei of the formula $-L-P$, wherein $-L-$ is selected from the group consisting of

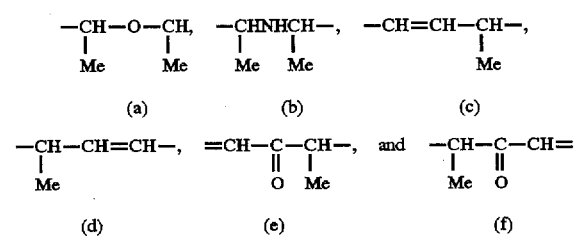

and P is a second Gp, which is one of the formulae 1–6 but lacks $R^4$ and is conjugated to L through the position shown as occupied by $R^4$, or another porphyrin group. When P is another porphyrin group, P preferably has the formula:

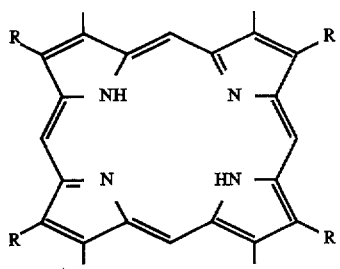

wherein each R is independently H or lower alkyl (1–4C);

two of the four bonds shown as unoccupied on adjacent rings are joined to $R^3$;

one of the remaining bonds shown as unoccupied is joined to $R^4$; and the other is joined to L;

with the proviso that, if $R^4$ is —CHCH$_2$, both $R^3$ groups cannot be carbalkoxyethyl. The preparation and use of such compounds is disclosed in U.S. Pat. Nos. 4,920,143 and 4,883,790, which are hereby incorporated by reference.

Figure 2A:
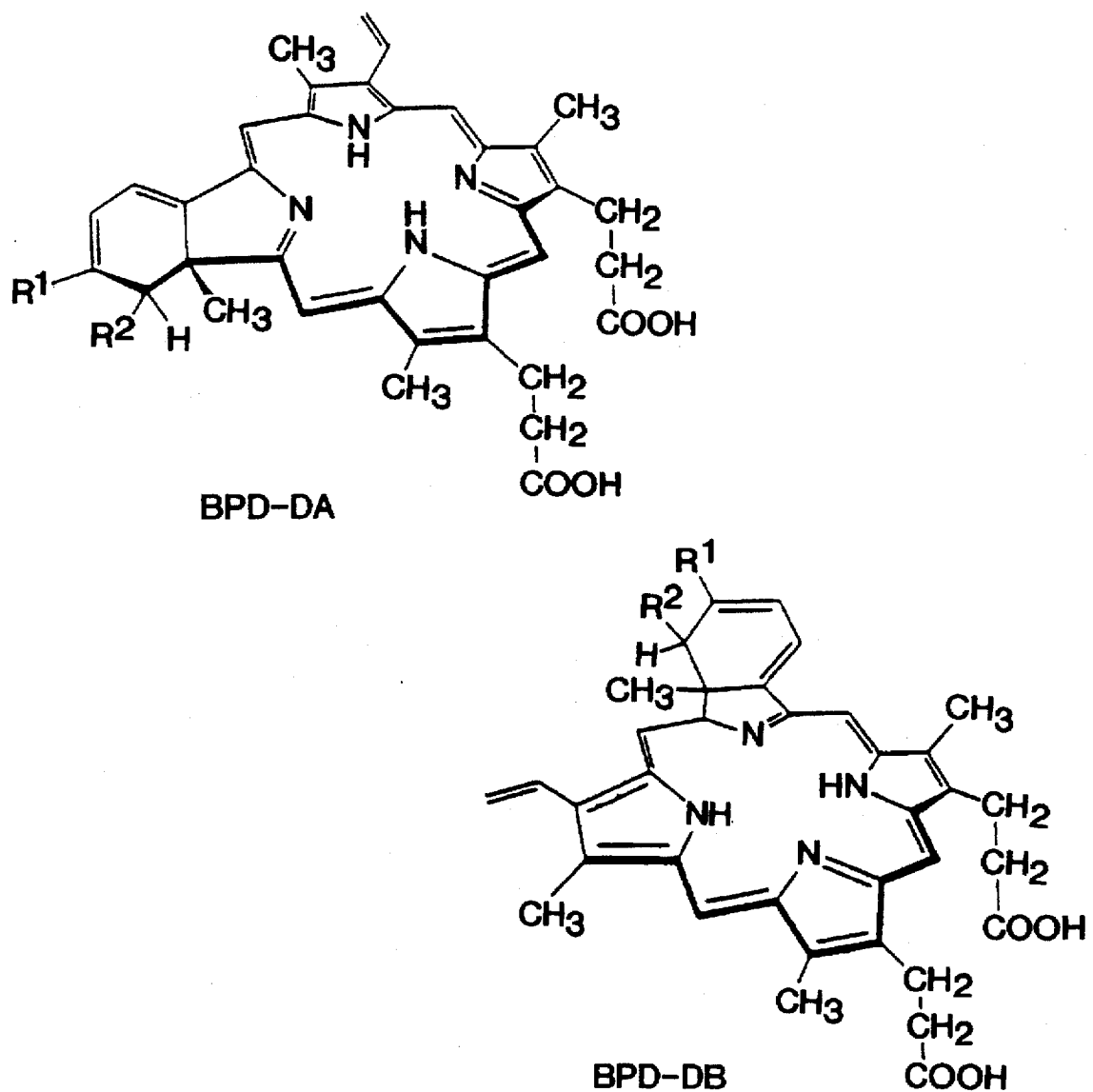
FIGS. 2(a–b) shows the structure of four preferred forms of the hydro-monobenzoporphyrin derivatives (BPD's) of formulas 3 and 4 in FIG. 1.
Figure 2B:
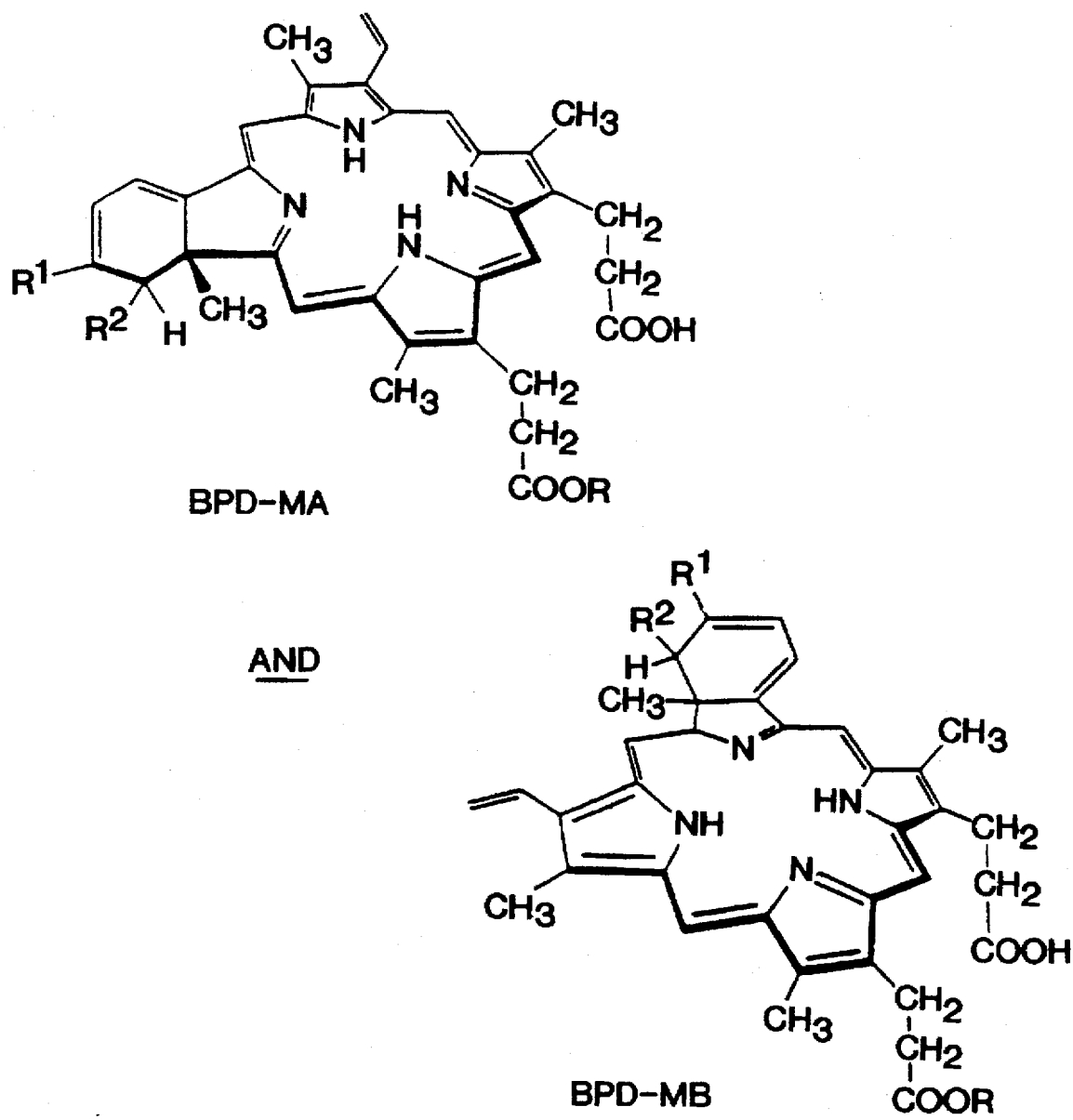

Even more preferred are hydro-monobenzoporphyrin compounds that are designated as benzoporphyrin derivatives ("BPD's"). BPD's are hydrolyzed forms, or partially hydrolyzed forms, of the rearranged products of formula 1–3 or formula 1–4, where one or both of the protected carboxyl groups of $R^3$ are hydrolyzed. Particularly preferred is the compound referred to as BPD-MA in FIG. 2, which has two equally active regioisomers.

Many desirable hydro-monobenzoporphyrin photosensitizers, such as BPD-MA, are not only insoluble in water at physiological pH's, but are also insoluble in (1) pharmaceutically acceptable aqueous-organic co-solvents, (2) aqueous polymeric solutions, and (3) surfactant/micellar solutions. However, such photosensitizers can still be "solubilized" in a form suitable for parenteral administration by using a liposome composition. For example, BPD-MA can be "solubilized" at a concentration of about 2.0 mg/ml in aqueous solution using an appropriate mixture of phospholipids to form encapsulating liposomes.

Lipids

The liposomes of the inventions comprise a mixture of the commonly encountered lipids dimyristoyl phosphatidyl choline ("DMPC") and egg phosphatidyl glycerol ("EPG"). The presence of DMPC is important because DMPC is the major component in the composition to form liposomes which can solubilize and encapsulate insoluble hydro-monobenzoporphyrin photosensitizers into a lipid bilayer. The presence of EPG is important because the negatively charged, polar head group of this lipid can prevent aggregation of the liposomes.

Other phospholipids, in addition to DMPC and EPG, may also be present. Examples of suitable additional phospholipids that may also be incorporated into the liposomes of the present invention include phosphatidyl cholines (PCs), including mixtures of dipalmitoyl phosphatidyl choline (DPPC) and distearoyl phosphatidyl choline (DSPC). Examples of suitable phosphatidyl glycerols (PGs) include dimyristoyl phosphatidyl glycerol (DMPG), DLPG and the like.

Other types of suitable lipids that may be included are phosphatidyl ethanolamines (PEs), phosphatidic acids (PAs), phosphatidyl serines, and phosphatidyl inositols.

The molar ratio of the hydro-monobenzoporphyrin photosensitizer to the DMPC/EPG phospholipid mixture can be as low as 1:7.0 or may contain a higher proportion of phospholipid, such as 1:7.5. Preferably, this molar ratio is 1:8 or more phospholipid, such as 1:10, 1:15, or 1:20. This molar ratio depends upon the exact photosensitizer being used, but will assure the presence of a sufficient number of DMPC and EPG lipid molecules to form a stable complex with most hydro-monobenzoporphyrin photosensitizer molecules. When the number of lipid molecules is not sufficient to form a stable complex, the lipophilic phase of the lipid bilayer becomes saturated with photosensitizer molecules. Then, any slight change in the process conditions can force some of the previously encapsulated photosensitizer to leak out of the vesicle, onto the surface of the lipid bilayer, or even out into the aqueous phase.

If the concentration of hydro-monobenzoporphyrin photosensitizer is high enough, it can actually precipitate out from the aqueous layer and promote aggregation of the liposomes. The more unencapsulated photosensitizer that is present, the higher the degree of aggregation. The more aggregation, the larger the mean particle size will be, and the more difficult aseptic or sterile filtration will be. Thus, as demonstrated in Example 1 below, even small changes in the molar ratio can be important in achieving the improved filterability sought in the invention.

Accordingly, slight increases in the lipid content can increase significantly the filterability of the liposome composition by increasing the ability to form and maintain small particles. This is particularly advantageous when working with significant volumes of 500 ml, a liter, five liters, 40 liters, or more, as opposed to smaller batches of about 100–500 ml or less. This volume effect is thought to occur because larger homogenizing devices tend to provide less efficient agitation than can be accomplished easily on a small scale. For example, a large size Microfluidizer™ has a less efficient interaction chamber than that one of a smaller size.

A molar ratio of 1.05:3:5 BPD-MA:EPG:DMPC (i.e., slightly less phospholipid than 1:8.0 photosensitizer:phospholipid) may provide marginally acceptable filterability in small batches of up to 500 ml. However, when larger volumes of the composition are being made, a higher molar ratio of phospholipid provides more assurance of reliable aseptic filterability. Moreover, the substantial potency losses that are common in scale-up batches, due at least in part to filterability problems, can thus be avoided.

Cryoprotective Agents and Isotonic Agents

Any cryoprotective agent known to be useful in the art of preparing freeze-dried formulations, such as di- or polysaccharides or other bulking agents such as lysine, may be used in the claimed invention. Further, isotonic agents typically added to maintain isomolarity with body fluids may be used. In a preferred embodiment, a di-saccharide or polysaccharide is used and functions both as a cryoprotective agent and as an isotonic agent.

In an especially preferred embodiment, the particular combination of the phospholipids, DMPC and EPG, and a disaccharide or polysaccharide form a liposomal composition having liposomes of a particularly narrow particle size distribution. When the process of hydrating a lipid film is prolonged, larger liposomes tend to be formed, or the photosensitizer can even begin to precipitate. The addition of a disaccharide or polysaccharide provides instantaneous hydration and the largest surface area for depositing a thin film of the drug-phospholipid complex. This thin film provides for faster hydration so that, when the liposome is initially formed by adding the aqueous phase, the liposomes formed are of a smaller and more uniform particle size. This provides significant advantages in terms of manufacturing ease.

However, it is also possible that, when a saccharide is present in the composition of the invention, it is added after dry lipid film formation, as a part of the aqueous solution used in hydration. In a particularly preferred embodiment, a saccharide is added to the dry lipid film of the invention during hydration.

Disaccharides or polysaccharides are preferred to monosaccharides for this purpose. To keep the osmotic pressure of the liposome composition of the invention similar to that of blood, no more than 4–5% monosaccharides could be added. In contrast, about 9–10% of a disaccharide can be used without generating an unacceptable osmotic pressure. The higher amount of disaccharide provides for a larger surface area, which results in smaller particle sizes being formed during hydration of the lipid film.

Accordingly, the preferred liposomal composition of the present invention comprises a disaccharide or polysaccharide, in addition to the photosensitizer and the mixture of DMPC and EPG phospholipids. When present, the disaccharide or polysaccharide is preferably chosen from among the group consisting of lactose, trehalose, maltose, maltotriose, palatinose, lactulose or sucrose, with lactose or trehalose being preferred. Even more preferably, the liposomes comprise lactose or trehalose.

Also, when present, the disaccharide or polysaccharide is formulated in a preferred ratio of about 10–20 saccharide to 0.5–6.0 DMPC/EPG phospholipid mixture, respectively, even more preferably at a ratio from about 10 to 1.5–4.0. In one embodiment, a preferred but not limiting formulation is lactose or trehalose and a mixture of DMPC and EPG in a concentration ratio of about 10 to 0.94–1.88 to about 0.65–1.30, respectively.

The presence of the disaccharide or polysaccharide in the composition not only tends to yield liposomes having extremely small and narrow particle size ranges, but also provides a liposome composition in which hydro-monobenzoporphyrin photosensitizers, in particular, may be stably incorporated in an efficient manner, i.e., with an encapsulation efficiency approaching 80–100%. Moreover, liposomes made with a saccharide typically exhibit improved physical and chemical stability, such that they can retain an incorporated hydro-monobenzoporphyrin photosensitizer compound without leakage upon prolonged storage, either as a reconstituted liposomal suspension or as a cryodesiccated powder.

Excipients

Other optional ingredients include minor amounts of nontoxic, auxiliary substances in the liposomal composition, such as antioxidants, e.g., butylated hydroxytoluene, alpha-tocopherol and ascorbyl palmitate; pH buffering agents, e.g., phosphates, glycine, and the like.

Preparation

Liposomes containing a selected hydro-monobenzoporphyrin photosensitizer as described herein may be prepared by combining the photosensitizer and the DMPC and EPG phospholipids (and any other optional phospholipids or excipients, such as antioxidants) in the presence of an organic solvent. Suitable organic solvents include any volatile organic solvent, such as diethyl ether, acetone, methylene chloride, chloroform, piperidine, piperidine-water mixtures, methanol, tert-butanol, dimethyl sulfoxide, N-methyl-2-pyrrolidone, and mixtures thereof. Preferably, the organic solvent is water-immiscible, such as methylene chloride, but water immiscibility is not required. In any event, the solvent chosen should not only be able to dissolve all of the components of the lipid film, but should also not react with, or otherwise deleteriously affect, these components to any significant degree.

The organic solvent is then removed from the resulting solution to form a dry lipid film by any known laboratory technique that is not deleterious to the dry lipid film and the photosensitizer. Preferably, the solvent is removed by placing the solution under a vacuum until the organic solvent is evaporated. The solid residue is the dry lipid film of the invention. The thickness of the lipid film is not critical, but usually varies from about 30 to about 45 mg/cm$^2$, depending upon the amount of solid residual and the total area of the glass wall of the flask. Once formed, the film may be stored for an extended period of time, preferably not more than 4 to 21 days, prior to hydration. While the temperature during a lipid film storage period is also not an important factor, it is preferably below room temperature, most preferably in the range from about −20 to about 4° C.

The dry lipid film is then dispersed in an aqueous solution, preferably containing a disaccharide or polysaccharide, and homogenized to form the desired particle size. Examples of useful aqueous solutions used during the hydration step include sterile water; a calcium- and magnesium-free, phosphate-buffered (pH 7.2–7.4) sodium chloride solution; a 9.75% w/v lactose solution; a lactose-saline solution; 5% dextrose solution; or any other physiologically acceptable aqueous solution of one or more electrolytes. Preferably, however, the aqueous solution is sterile. The volume of aqueous solution used during hydration can vary greatly, but should not be so great as about 98% nor so small as about 30–40%. A typical range of useful volumes would be from about 75% to about 95%, preferably about 85% to about 90%.

Upon hydration, coarse liposomes are formed that incorporate a therapeutically effective amount of the hydro-monobenzoporphyrin photosensitizer-phospholipid complex. The "therapeutically effective amount" can vary widely, depending on the tissue to be treated and whether it is coupled to a target-specific ligand, such as an antibody or an immunologically active fragment. It should be noted that the various parameters used for selective photodynamic therapy are interrelated. Therefore, the therapeutically effective amount should also be adjusted with respect to other parameters, for example, fluence, irradiance, duration of the light used in photodynamic therapy, and the time interval between administration of the photosensiting agent and the therapeutic irradiation. Generally, all of these parameters are adjusted to produce significant damage to tissue deemed undesirable, such as neovascular or tumor tissue, without significant damage to the surrounding tissue, or to enable the observation of such undesirable tissue without significant damage to the surrounding tissue.

Typically, the therapeutically effective amount is such to produce a dose of hydro-monobenzoporphyrin photosensitizer within a range of from about 0.1 to about 20 mg/kg, preferably from about 0.15–2.0 mg/kg and, even more preferably, from about 0.25 to about 0.75 mg/kg. Preferably, the w/v concentration of the photosensitizer in the composition ranges from about 0.1 to about 8.0–10.0 g/L, when the mixture becomes such a thick gel that it is not possible to handle or administer to a subject by the usual means. Most preferably, the concentration is about 2.0 to 2.5 g/L.

The hydration step should take place at a temperature that does not exceed about 30° C., preferably below the glass transition temperature of the photosensitizer-phospholipid complex formed, even more preferably at room temperature or lower, e.g., 15°–20° C. The glass transition temperature of the photosensitizer-lipid complex can be measured by using a differential scanning microcalorimeter.

In accordance with the usual expectation that the aqueous solubility of a substance should increase as higher temperatures are used, at a temperature around the transition temperature of the complex, the lipid membrane tends to undergo phase transition from a "solid" gel state to a pre-transition state and, finally, to a more "fluid" liquid crystal state. At these higher temperatures, however, not only does fluidity increase, but the degree of phase separation and the proportion of membrane defects also increases. This results in an increasing degree of leakage of the photosensitizer from inside the membrane to the interface and even out into the aqueous phase. Once a significant amount of liposome leakage has occurred, even slight changes in the conditions such as a small drop in temperature, can shift the equilibrium away from aqueous "solubility" in favor of precipitation of the photosensitizer. Moreover, once the typically water-insoluble photosensitizer begins to precipitate, it is not possible to re-encapsulate it within the lipid bilayer. The precipitate is thought to contribute significantly to filterability problems.

In addition, the usual thickness of a lipid bilayer in the "solid" gel state (about 47 Å) decreases in the transition to the "liquid" crystalline state to about 37 Å, thus shrinking the entrapped volume available for the hydro-monobenzoporphyrin photosensitizer to occupy. The smaller "room" is not capable of containing as great a volume of photosensitizer, which can then be squeezed out of the saturated lipid bilayer interstices. Any two or more vesicles in the process of exuding photosensitizer may aggregate together, introducing further difficulties with respect to particle size reduction and ease of sterile filtration. See FIG. 4 for an illustration of one proposed mechanism to explain this surprising effect of temperature on photosensitizer liposome aggregation. Moreover, the use of higher hydration temperatures, such as, for example, about 35° to 45° C., can also result in losses of photosensitizer potency as the photosensitizer either precipitates or aggregates during aseptic filtration.

The particle sizes of the coarse liposomes first formed in hydration are then homogenized to a more uniform size, reduced to a smaller size range, or both, to about 150 to 300 nm, preferably also at a temperature that does not exceed about 30° C., preferably below the glass transition temperature of the photosensitizer-phospholipid complex formed in the hydration step, and even more preferably below room temperature of about 25° C. Various high-speed agitation devices may be used during the homogenization step, such as a Microfluidizer™, for example a Microfluidics™ Model 110F; a sonicator; a high-shear mixer; a homogenizer; or a standard laboratory shaker.

It has been found that the homogenization temperature should be at room temperature or lower, e.g., 15°-20° C. At higher homogenization temperatures, such as about 32°-42° C., the relative filterability of the liposome composition may improve initially due to increased fluidity as expected, but then, unexpectedly, tends to decrease with continuing agitation due to increasing particle size.

Preferably, a high pressure device such as a Microfluidizer™ is used for agitation. In microfluidization, a great amount of heat is generated during the short period of time during which the fluid passes through a high pressure interaction chamber. In the interaction chamber, two streams of fluid at a high speed collide with each other at a 90° angle. As the microfluidization temperature increases, the fluidity of the membrane also increases, which initially makes particle size reduction easier, as expected. For example, filterability can increase by as much as four times with the initial few passes through a Microfluidizer™ device. The increase in the fluidity of the bilayer membrane promotes particle size reduction, which makes filtration of the final composition easier. In the initial several passes, this increased fluidity mechanism advantageously dominates the process.

However, as the number of passes and the temperature both increase, more of the hydrophobic hydro-monobenzoporphyrin photosensitizer molecules are squeezed out of the liposomes, increasing the tendency of the liposomes to aggregate into larger particles. At the point at which the aggregation of vesicles begins to dominate the process, the sizes cannot be reduced any further. Surprisingly, particle sizes actually then tend to grow through aggregation.

For this reason, in the method of the invention, the homogenization temperature is cooled down to and maintained at a temperature no greater than room temperature after the composition passes through the zone of maximum agitation, e.g., the interaction chamber of a Microfluidizer™ device. An appropriate cooling system can easily be provided for any standard agitation device in which homogenization is to take place, e.g., a Microfluidizer™, such as by circulating cold water into an appropriate cooling jacket around the mixing chamber or other zone of maximum turbulence. While the pressure used in such high pressure devices is not critical, pressures from about 10,000 to about 16,000 psi are not uncommon.

As a last step, the compositions of the inventions are preferably aseptically filtered through a filter having an extremely small pore size, i.e., 0.22 μm. Filter pressures used during sterile filtration can vary widely, depending on the volume of the composition, the density, the temperature, the type of filter, the filter pore size, and the particle size of the liposomes. However, as a guide, a typical set of filtration conditions would be as follows: filtration pressure of 15–25 psi; filtration load of 0.8 to 1.5 ml/cm$^2$; and filtration temperature of about 25° C.

A typical general procedure is described below with additional exemplary detail:

(1) Sterile filtration of organic solvent through a hydrophobic, 0.22 μm filter.

(2) Addition of EPG, DMPC, hydro-monobenzoporphyrin photosensitizer, and excipients to the filtered organic solvent, dissolving both the excipients and the photosensitizer.

(3) Filtration of the resulting solution through a 0.22 μm hydrophobic filter.

(4) Transfer of the filtrate to a rotary evaporator apparatus, such as that commercially available under the name Rotoevaporator™.

(5) Removal of the organic solvent to form a dry lipid film.

(6) Analysis of the lipid film to determine the level of organic solvent concentration.

(7) Preparation of a 10% lactose solution.

(8) Filtration of the lactose solution through a 0.22 μm hydrophilic filter.

(9) Hydration of the lipid film with a 10% lactose solution to form coarse liposomes.

(10) Reduction of the particle sizes of the coarse liposomes by passing them through a Microfluidizer™ three times.

(11) Determination of the reduced particle size distribution of liposomes.

(12) Aseptic filtration of the liposome composition through a 0.22 μm hydrophilic filter. (Optionally, the solution may first be pre-filtered with a 5.0 μm prefilter.)

(13) Analysis of photosensitizer potency.

(14) Filling of vials with the liposome composition.

(15) Freeze-drying.

Freeze-drying

Once formulated, the liposome composition of the invention may be freeze-dried for long-term storage if desired. For example, BPD-MA, a preferred hydro-monobenzoporphyrin photosensitizer, has maintained its potency in a cryodesiccated liposome composition for a period of at least nine months at room temperature, and a shelf life of at least two years has been projected. If the composition is freeze-dried, it may be packed in vials for subsequent reconstitution with a suitable aqueous solution, such as sterile water or sterile water containing a saccharide and/or other suitable excipients, prior to administration, for example, by injection.

Preferably, liposomes that are to be freeze-dried are formed upon the addition of an aqueous vehicle contain a disaccharide or polysaccharide during hydration. The composition is then collected, placed into vials, freeze-dried, and stored, ideally under refrigeration. The freeze-dried composition can then be reconstituted by simply adding water for injection just prior to administration.

Particle Size

The liposomal composition of the present invention provides liposomes of a sufficiently small and narrow particle size that the aseptic filtration of the composition through a 0.22 μm hydrophilic filter can be accomplished efficiently and with large volumes of 500 ml to a liter or more without significant clogging of the filter. A particularly preferred particle size range is below about 300 nm, more preferably below from about 250 nm. Most preferably, the particle size is below about 220 nm.

As seen above, the invention controls three major parameters that can affect the ease of particle size reduction to an unexpected degree. As a result, the filterability, particularly with standard aseptic filtration, is significantly improved in the liposome composition of the invention. These parameters are (1) suitable molar ratio of hydro-monobenzoporphyrin photosensitizer to DMPC-EPG lipid mixture; (2) temperature during the hydration step; and (3) temperature during the homogenization or size reduction step. Of these three factors, the photosensitizer/lipid molar ratio appears to have the greatest effect.

Filterability can be tested by passing a liposome composition through a Microfluidizer™ three times and withdrawing a sample with a syringe. The syringe is connected to a 0.22 μm hydrophilic filter and then placed in a syringe pump. The constant rate of piston movement is set at 10 ml/min, and filtrate is collected until the filter becomes blocked by large aggregates of liposome. The volume of the filtrate is then measured and recorded in terms of ml/cm$^2$ or g/cm$^2$, with a square centimeter being the effective filtration area. Thus, filterability for the purposes of the invention is defined as the maximum volume or weight of liposomal composition that can be filtered through a 0.22 μm filter.

Administration and Use

The use of the hydro-monobenzoporphyrin photosensitizers incorporated in the liposomes of the invention is typically for the diagnosis or treatment of cancer. The liposomal compositions are useful in sensitizing neoplastic cells or other abnormal tissue, including infectious agents, to destruction by exposure with light, preferably, visible light. Upon photoactivation, the photosensitizer thought to promote the formation of singlet oxygen, which is responsible for the cytotoxic effect. By incorporating the photosensitizer in the liposomes of the present invention, more efficient sensitization of tumor tissues can be obtained.

In addition, when the photosensitizers of the invention are photoactivated by appropriate excitation wavelengths, they are typically able to fluoresce visibly. This fluorescence can then be used to localize the tumor or other target tissue.

Generally speaking, the concentration of the hydro-monobenzoporphyrin photosensitizer in the liposome depends upon the nature of the photosensitizer used. When BPD-MA is used, for example, the photosensitizer is generally incorporated in the liposomes at a concentration of about 0.10% up to 0.5% w/v. If freeze-dried and reconstituted, this would typically yield a reconstituted solution of up to about 5.0 mg/ml photosensitizer.

The liposome compositions of the invention are typically administered parenterally. Injection may be intravenous, subcutaneous, intramuscular, intrathecal, or even intraperitoneal. However, the liposomes could also be administered by aerosol intranasally or intrapulmonarally.

The quantity of hydro-monobenzoporphyrin photosensitizer liposome formulations to be administered depends on the choice of active ingredients, the conditions to be treated, the mode of administration, the individual subject, and the judgement of the practitioner. Generally speaking, however, dosages in the range of 0.05–10 mg/kg may be needed. The foregoing range is, of course, merely suggestive, as the number of variables in regard to an individual treatment regime is large. Therefore, considerable excursions from these recommended values are expected.

For use as a diagnostic in localizing tumor tissue or in localizing atherosclerotic plaques, the pharmaceutical compositions of the invention are administered systemically in the same general manner as is known with respect to photodynamic therapy. The waiting period to allow the drugs to clear from tissues to which they do not accumulate is approximately the same, for example, from about 30 minutes to about 10 hours. After the compositions of the invention have been permitted to localize, the location of the target tissue is determined by detecting the presence of the photosensitizer.

For diagnosis, the hydro-monobenzoporphyrin photosensitizer compounds incorporated into liposomes may be used along with, or may be labeled with, a radioisotope or other detecting means. If this is the case, the detection means depends on the nature of the label. Scintigraphic labels such as technetium or indium can be detected using ex vivo scanners. Specific fluorescent labels can also be used but, like detection based on fluorescence of the photosensitizers themselves, these labels can require prior irradiation.

For activation of the photosensitizer hydro-monobenzoporphyrin of the invention, any suitable absorption wavelength is used. This can be supplied using the various methods known to the art for mediating cytotoxicity or fluorescence emission, such as visible radiation, including incandescent or fluorescent light sources or photodiodes such as light emitting diodes. Laser light can also be used for in situ delivery of light to a localized photosensitizer. In a typical protocol, for example, several hours prior to irradiation, approximately 0.5–1.5 mg/kg of a green porphyrin photosensitizer is injected intravenously and then excited by an appropriate wavelength.

The methods of preparing the liposomal compositions of the present invention, the compositions themselves, and the method of using them in photodynamic treatment are described in greater detail in the examples below. These examples are readily adapted to the production and use of analogously described liposomes by simple substitutions of appropriate hydro-monobenzoporphyrin photosensitizers, additional phospholipids or alternative methods. The following examples are being presented to describe the preferred embodiments, utilities and attributes of the present invention, but they not meant to limit the invention. For example, although BPD-MA is used as the hydro-monobenzoporphyrin photosensitizer to form liposomes, the invention is not intended to be limited to this particular photosensitizer.

EXAMPLE 1

Effect of Molar Ratio on Filterability

Three 100-ml batches of BPD-MA liposomes were prepared at room temperature (about 20° C.), using the following general procedure. BPD-MA, butylated hydroxytoluene ("BHT"), ascorbyl palmirate, and the phospholipids DMPC and EPG were dissolved in methylene chloride, and the resulting solution was filtered through a 0.22 μm filter. The solution was then dried under vacuum using a rotary evaporator until the amount of methylene chloride in the solid residue was not detectable by gas chromatography.

A 10% lactose/water-for-injection solution was then prepared and filtered through a 0.22 μm filter. The lactose/water solution was added to the flask containing the solid residue of the photosensitizer/phospholipid. The solid residue was dispersed in the 10% lactose/water solution and stirred for about one hour, cooled, and passed through a homogenizer. The solution was then filtered through a 0.22 μm Durapore, hydrophilic filter.

Using the foregoing procedure, three different preparations of the BPD-MA liposomal composition, each having a different molar ratio of photosensitizer:EPG:DMPC, was prepared as follows:

TABLE 1

| | Formulations | | |
|---|---|---|---|
| Components | Molar Ratio 1.05:3:5 | Molar Ratio 1.0:3:5 | Molar Ratio 1.0:3:7 |
| Photosensitizer | 0.21 g | 0.21 g | 0.21 g |
| EPG | 0.65 g | 0.68 g | 0.68 g |
| DMPC | 0.94 g | 0.99 g | 1.38 g |
| Butylated hydroxy toluene ("BHT") | 0.0002 g | 0.0002 g | 0.0002 g |
| Ascorbic acid 6-palmitate | 0.002 g | 0.002 g | 0.002 g |
| Lactose NF crystalline injectable | 10 g | 10 g | 10 g |
| Water for injection qs | 100 ml | 100 ml | 100 ml |

The filterability of these three batches was tested according to the following method: After the liposome composition had been passed three times through a Microfluidize™, a sample was withdrawn with a syringe. The volume of the sample withdrawn depended on a visual estimation of the filterability of the composition. The syringe was connected to a 0.22 μm hydrophilic filter and was then placed in a syringe pump. The rate of piston movement was set at 10 ml/min, and filtrate was collected until the filter became blocked by large liposome aggregates. The volume of the filtrate was measured and recorded as ml/cm². The results are summarized below in Table 2.

TABLE 2

| Formulations (BPD-MA: EPG:DMPC) | Total Lipid Concentration (% w/v) | Filterability (g/cm²) |
|---|---|---|
| Molar Ratio 1.05:3:5 | 1.59 | 1.57 |
| Molar Ratio 1.0:3:5 | 1.67 | 3.58 |
| Molar Ratio 1.0.:3:7 | 2.06 | 12.6 |

Figure 3:
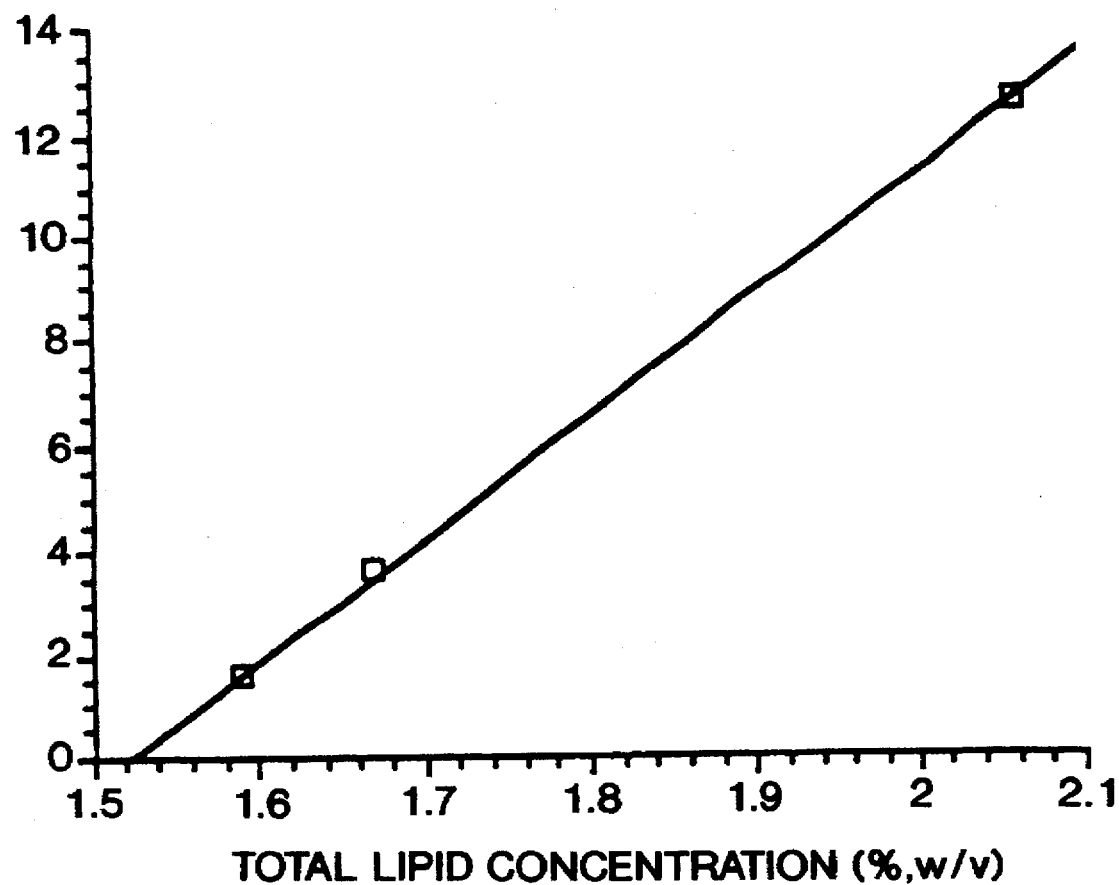
FIGS. 3(a–b) is a graphic representation of the relationship of filterability to lipid concentration.

Table 1 indicates that the filterability of the first formulation (slightly less phospholipid than a 1:8.0 photosensitizer/DMPC-EPG lipid mixture) was about 2.3 times less than the second formulation (which had a molar ratio of 1:8.0) and about eight times less than the 1:10.0 molar ratio of the third formulation. FIG. 3 shows a plot of the filterability in g/cm² versus total lipid concentration (%, w/v). The relationship was surprisingly linear, with an r-square of 0.9985. The following empirical equation was obtained from this plot:

$$\text{Filterability} = [23.36 \text{ Total Lipid Concentration} (\%, w/v)] - [35.51]$$

According to the slope of this equation, for every one-gram increase in DMPC or EPG lipid present, a 23-fold improvement in the filterability of the liposome formulation was achieved. The plot further indicates that, if the total lipid concentration became less than 1.52% with a BPD-MA photosensitizer concentration of 2.1 mg/ml, the liposome composition would not be capable of filtration through a 0.22 μm filter at all.

EXAMPLE 2

Filterability and Potency of Scale-up Batch

A larger batch of BPD-MA liposomes (1.2 liters, i.e., 12 times the 100-ml batches of Example 1) was prepared using the molar ratio 1:3:5 (photosensitizer:EPG:DMPC) at room temperature (about 20° C.). The contents of composition is described below in Table 3:

TABLE 3

| Components | Amount | Molar Ratio | No. of Moles | Molecular Weight |
|---|---|---|---|---|
| BPD-MA | 2.60 g | 1 | 0.00362 | 718 |
| EPG | 8.38 g | 3 | 0.01086 | 772 |
| DMPC | 12.26 g | 5 | 0.01811 | 677 |
| BHT | 0.0024 g | — | — | — |
| Ascorbic Acid 6-Palmitate | 0.024 g | — | — | — |
| Lactose NF Crystalline Injectable | 120 g | — | — | — |
| Water for Injection qs | 1.2 liters | — | — | — |

A double thickness of lipid film was used in this larger batch to provide a more strenuous test of the molar ratio of 1:8.0.

The results showed a significant improvement in filterability, as compared with a batch 1/12th the size with only slightly less of the DMDC and EPG lipids, as seen below in Table 4:

TABLE 4

| Formulations (BPD-MA:PG:DMPC) | Batch Size (ml) | Filterability (g/cm²) | Potency Pre-filtration | Potency Post-filtration |
|---|---|---|---|---|
| Molar ratio 1.05:3:5 | 100 | 1.57 | 2.11 | 2.10 |
| Molar ratio 1:3:5 | 100 | 3.58 | 2.05 | 2.02 |
| Molar ratio 1:3:7 | 100 | 12.60 | 2.11 | 2.23 |
| Molar ratio 1:3:5 | 1,200 | 5.00 | 2.09 | 2.08 |

The slight increase in lipid content greatly increased the filterability of the liposome composition. Moreover, the yield was nearly 100%, with a 99.5% (by HPLC analysis) photosensitizer potency being maintained after sterile filtration.

EXAMPLE 3

Hydration Temperature

Four batches of BPD-MA liposome compositions, each having the same photosensitizer/DMPC-EPG lipid molar ratio (1.05:3:5), were prepared using different film hydration temperatures. Data for these four batches, presented below in Table 5, were compared to demonstrate the relationship of potency loss and film hydration temperature.

TABLE 5

| Batch | Hydration Temperature (°C.) | Potency Loss (%) |
|---|---|---|
| 1 | 30 | 9.5 |
| 2 | Room temperature (about 25° C.) | 4.8 |
| 3 | 30 | 16.7 |
| 4 | 40 | 85.0 |

The results showed that an increase in hydration temperature above room temperature was associated with an undesirable, significant loss in the potency of the photosensitizer.

EXAMPLE 4

Effect of Rising Homogenization Temperature

A pair of 0.53-liter batches (photosensitizer:EPG:DMPC= 1.05:3:5) was used to study the relationship between filterability and homogenization temperature. The compositions were prepared as described above in Example 1 using a hydration temperature of 45° C. and a Microfluidizer™ with the outlet temperature set at 35° C. The data showed that, at high hydration and homogenization temperatures, the relative filterability of BPD-MA liposome compositions increased after the initial passes through a Microfluidizer™ (#1 to #2), as expected, but then decreased for additional passes (#2 to #4), as seen below:

TABLE 6

| Pass # | Filterability (ml/cm²) |
|---|---|
| 1 | 0.10 |
| 2 | 0.27 |
| 3 | 0.22 |
| 4 | 0.19 |

The second 0.53-liter batch (photosensitizer:EPG:DMPC=1.05:3:5) was used to study the relationship between the number of passes through a Microfluidizer™, filterability, and particle size distribution. In this batch, both a high hydration temperature (40° C.) and a high homogenization temperature (Microfluidizer™ outlet temperature set at 42° C.) were used. The data is listed below in Table 7.

TABLE 7

| Pass # | Filterability (ml/cm²) | Particle Size Distribution (+50 nm) |
|---|---|---|
| 1 | N/A | 710 |
| 2 | N/A | 710 |
| 3 | 0.25 | 265 |
| 4 | 0.25 | 250 |
| 5 | 0.50 | 250 |
| 6 | 0.50 | 247 |
| 7 | 0.30 | 302 |
| 8 | 0.25 | 302 |
| 9 | 0.25 | 295 |

The data show that the filterability increased from passes #3 to #5, as expected, but then dropped back to the original value in passes #6 to #9. In contrast, the average particle size of the liposomes in the composition was reduced from 710 nm at pass #1 to as small as 247 nm at pass #6. However, as additional passes were made, the particle size unexpectedly increased to about 300 nm.

EXAMPLE 5

Preparation of Liposomes of the Invention

A 100-ml batch of BPD-MA liposomes is prepared at room temperature (about 20° C.) using the following general procedure. BPD-MA, butylated hydroxytoluene ("BHT"), ascorbyl palmitate, and the phospholipids DMPC and EPG are dissolved in methylene chloride. The molar ratio of photosensitizer:EPG:DMPC is 1.0:3:7 and has the following composition:

| | |
|---|---|
| Photosensitizer | 0.21 g |
| EPG | 0.68 g |
| DMPC | 1.38 g |
| BHT | 0.0002 g |
| Ascorbic acid 6-palmitate | 0.002 g |
| Lactose NF crystalline injectable | 10 g |
| Water for injection qs | 100 ml |

Using the above formulation, the total lipid concentration (% w/v) is about 2.06. The resulting solution is filtered through a 0.22 μm filter and then dried under vacuum using a rotary evaporator. Drying is continued until the amount of methylene chloride in the solid residue is no longer detectable by gas chromatography.

A 10% lactose/water-for-injection solution is then prepared and filtered through a 0.22 μm filter. Instead of being warmed to a temperature of about 35° C., the lactose/water solution is allowed to remain at room temperature (about 25° C.) for addition to the flask containing the solid residue of the photosensitizer/phospholipid. The solid residue is dispersed in the 10% lactose/water solution at room temperature, stirred for about one hour, and passed through a Microfluidizer™ homogenizer three to four times with the outlet temperature controlled to about 20°–25° C. The solution is then filtered through a 0.22 μm Durapore, hydrophilic filter.

The filterability of the batch is tested by the following procedure: After the liposome composition has been passed three times through a Microfluidizer™, a sample is withdrawn with a syringe. The volume of the sample withdrawn is about 20 ml, depending on a visual estimation of the filterability of the composition and assessment of the quality of the liposomes. The syringe is connected to a 0.22 μm hydrophilic filter and is then placed in a syringe pump. The rate of piston movement is set at 10 ml/min, and filtrate is collected until the filter becomes blocked by large liposome aggregates. The filtrate is measured and recorded as ml/cm² or g/cm².

The filterability of the composition in g/cm² is typically greater than about 10. Moreover, the yield is about 100% by HPLC analysis, with photosensitizer potency typically being maintained even after sterile filtration. Average particle sizes vary from about 150 to about 300 nm (±50 nm).

It will be clear to those skilled in the art that modifications and/or variations of the disclosed subject matter can be made without departing from the scope of the invention claimed below.

We claim:

1. A method for making a pharmaceutical composition containing liposomes, said liposomes comprising a therapeutically acceptable amount of a hydro-monobenzoporphyrin photosensitizer and a mixture of phospholipids comprising egg phosphatidyl glycerol ("EPG") and dimyristoyl phosphatidyl choline ("DMPC"), wherein said method comprises the steps of:
    a. combining the photosensitizer and the phospholipids in a molar ratio of 1:7.0 or more phospholipid in the presence of an organic solvent;
    b. removing said organic solvent to form a photosensitizer:phospholipid complex;
    c. hydrating said photosensitizer:phospholipid complex with an aqueous solution at a temperature below the glass transition temperature of the photosensitizer:phospholipid complex to form coarse liposomes containing said photosensitizer-phospholipid complex; and
    d. homogenizing or reducing the particle size of said coarse liposomes to a particle size range of below about 300 nm at a temperature below the glass transition temperature of the photosensitizer:phospholipid complex.

2. The method of claim 1, wherein said molar ratio of hydro-monobenzoporphyrin photosensitizer to phospholipids is about 1:8.0 or more phospholipid.

3. The method of claim 1, wherein said organic solvent is methylene chloride.

4. The method of claim 1, wherein said organic solvent is removed in step "b." by evaporation under reduced pressure.

5. The method of claim 1, wherein said aqueous solution comprises a disaccharide or polysaccharide.

6. The method of claim 4, wherein said disaccharide or polysaccharide is selected from lactose or trehalose.

7. The method of claim 4, wherein the concentration ratio of disaccharide or polysaccharide to said mixture of phospholipids is about 10–20 to 0.5–6.0.

8. The method of claim 1, wherein said hydro-monobenzoporphyrin (Gp) photosensitizer has one of the formulae 1–6 set forth in FIG. 1 and has one or more light absorption maxima between 670–780 nm, or is a metalated or labeled form thereof,
wherein
    each $R^1$ and $R^2$ is independently selected from the group consisting of carbalkoxy (2–6C), alkyl (1–6C) sulfonyl, aryl (6–10C) sulfonyl, aryl (6–10C), cyano, and —CONR⁵CO— wherein $R^5$ is aryl (6–10C) or alkyl (1–6C);
    each $R^3$ is independently carboxyalkyl (2–6C) or a salt, amide, ester or acylhydrazone thereof, or is alkyl (1–6C); and
    $R^4$ is —CHCH₂; —CHOR⁴' wherein $R^{4'}$ is H or alkyl (1–6C), optionally substituted with a hydrophilic substituent; —CHO; —COOR⁴'; —CH(OR⁴')CH₃; —CH(OR⁴')CH₂OR⁴'; —CH(SR⁴')CH₃; —CH(NR⁴'₂)CH₃; —CH(CN)CH₃; —CH(COOR⁴')CH₃; —CH(OOCR⁴')CH₃; —CH(halo)CH₃; —CH(halo)CH₂(halo); an organic group of less than 12C resulting from direct or indirect derivatization of a vinyl group; or $R^4$ is a 1–3 tetrapyrrole-type nucleus of the formula —L—P, wherein —L— is selected from the group consisting of

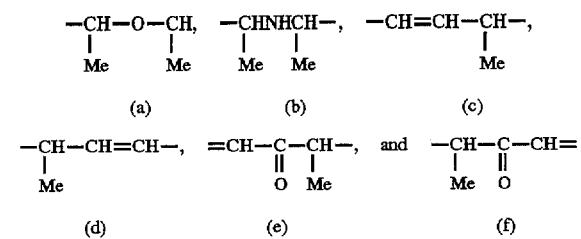

and P is a second Gp, which is one of the formulae 1–6 but lacks $R^4$ and is conjugated to L through the position shown as occupied by $R^4$, or another porphyrin group.

9. The method of claim 8 wherein, when P is said another porphyrin group, P has the formula:

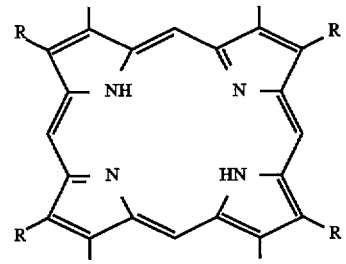

wherein:
    each R is independently H or lower alkyl (1–4C);
    two of the four bonds shown as unoccupied on adjacent rings are joined to $R^3$;
    one of the remaining bonds shown as unoccupied is joined to $R^4$; and
    the other is joined to L;

with the proviso that, if $R^4$ is $CHCH_2$, said $R^3$ groups cannot both be carbalkoxyethyl.

10. The method of claim 8, wherein each $R^3$ is —$CH_2CH_2COOH$ or salt, amide, ester or acylhydrazone thereof.

11. The method of claim 8, wherein each of $R^1$ and $R^2$ is carbalkoxy (2–6C).

12. The method of claim 1, wherein the photosensitizer is BPD-MA having the formula of FIG. 2.

13. The method of claim 1, wherein said hydrating step "c." is accomplished at a temperature at or below room temperature.

14. The method of claim 1, wherein said homogenizing or reducing step "d." is accomplished at a temperature at or below room temperature.

15. The method of claim 1, wherein said particle size is reduced to a range of below about 250 nm.

16. The method of claim 15 wherein the particle size is reduced to below about 220 nm.

17. A pharmaceutical composition containing liposomes in the particle size range of about 150 to 300 nm, wherein said liposomes comprise:
   a. a therapeutically acceptable amount of a photosensitizer and
   b. a mixture of phospholipids comprising:
      (1) egg phosphatidyl glycerol ("EPG") and
      (2) dimyristoyl phosphatidyl choline ("DMPC"), wherein the molar ratio of said photosensitizer and said mixture of phospholipids is about 1:7.0 or more phospholipid.

18. The composition of claim 17, wherein said molar ratio of photosensitizer to said mixture of phospholipids is about 1:8.0 or more phospholipid.

19. The composition of claim 17, wherein said hydromonobenzoporphyrin (Gp) has one of the formulae 1–6 set forth in FIG. 1 and has one or more light absorption maxima between 670–780 nm, or is a metalated or labeled form thereof, wherein:

each $R^1$ and $R^2$ is independently selected from the group consisting of carbalkoxy (2–6C), alkyl (1–6C) sulfonyl, aryl (6–10C) sulfonyl, aryl (6–10C), cyano, and —$CONR^5CO$— wherein $R^5$ is aryl (6–10C) or alkyl (1–6C);

each $R^3$ is independently carboxyalkyl (2–6C) or a salt, amide, ester or acylhydrazone thereof, or is alkyl (1–6C); and $R^4$ is —$CHCH_2$; —$CHOR^{4'}$ wherein $R^{4'}$ is H or alkyl (1–6C), optionally substituted with a hydrophilic substituent; —CHO; —$COOR^{4'}$; —$CH(OR^{4'}{}_2)CH_3$; —$CH(OR^{4'})CH_2OR^{4'}$; —$CH(SR^{4'})CH_3$; —$CH(NR^{4'})CH_3$; —$CH(CN)CH_3$; —$CH(COOR^{4'})CH_3$; —$CH(OOCR^{4'})CH_3$; —$CH(halo)CH_3$; —$CH(halo)CH_2(halo)$; an organic group of less than 12C resulting from direct or indirect derivatization of a vinyl group; or $R^4$ is a 1–3 tetrapyrrole-type nucleus of the formula —L—P, wherein —L— is selected from the group consisting of

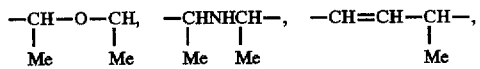

(a)  (b)  (c)

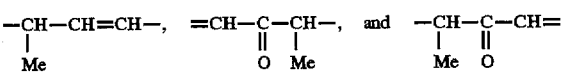

(d)  (e)  (f)

and P is a second Gp, which is one of the formulae 1–6 but lacks $R^4$ and is conjugated to L through the position shown as occupied by $R^4$, or another porphyrin group.

20. The composition of claim 19 wherein, when P is said another porphyrin group, it has the formula:

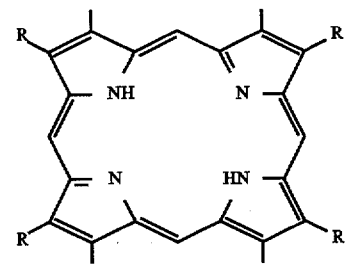

wherein each R is independently H or lower alkyl (1–4C);

two of the four bonds shown as unoccupied on adjacent rings are joined to $R^3$;

one of the remaining bonds shown as unoccupied is joined to $R^4$; and the other is joined to L;

with the proviso that, if $R^4$ is $CHCH_2$, said $R^3$ groups cannot both be carbalkoxyethyl.

21. The composition of claim 20, wherein each $R^3$ is —$CH_2CH_2COOH$ or a salt, amide, ester or acylhydrazone thereof.

22. The composition of claim 19, wherein each of $R^1$ and $R^2$ is carbalkoxy (2–6C).

23. The composition of claim 19, wherein the hydromonobenzoporphyrin photosensitizer is BPD-MA having the formula of FIG. 2.

24. The composition of claim 19, wherein said particle size is below about 220 nm.

* * * * *